United States Patent [19]
Goble et al.

[11] Patent Number: 5,354,300
[45] Date of Patent: Oct. 11, 1994

[54] DRILL GUIDE APPARATUS FOR INSTALLING A TRANSVERSE PIN

[75] Inventors: E. Marlowe Goble, Logan, Utah; Jerry L. Lower, Bourbon, Ind.

[73] Assignee: Depuy Inc., Warsaw, Ind.

[21] Appl. No.: 4,958

[22] Filed: Jan. 15, 1993

[51] Int. Cl.5 .............................................. A61F 5/04
[52] U.S. Cl. ...................................... 606/80; 606/98; 606/102; 606/104
[58] Field of Search .................. 606/98, 97, 96, 72, 606/73, 75, 102, 104, 80, 86, 87; 623/13; 408/241 G

[56] References Cited

U.S. PATENT DOCUMENTS

| | | | |
|---|---|---|---|
| 4,738,255 | 4/1988 | Goble et al. | |
| 4,772,286 | 9/1988 | Goble et al. | 623/13 |
| 4,883,048 | 11/1989 | Purnell et al. | 606/96 |
| 4,901,711 | 2/1990 | Goble et al. | 606/98 |
| 4,920,958 | 5/1990 | Walt et al. | 606/96 |
| 4,950,270 | 8/1990 | Bowman et al. | 606/72 |
| 4,952,213 | 8/1990 | Bowman et al. | 606/79 |
| 4,985,032 | 1/1991 | Goble | 606/96 |
| 5,013,316 | 5/1991 | Goble et al. | 606/72 |
| 5,112,337 | 5/1992 | Paulos et al. | 606/96 |
| 5,152,764 | 10/1992 | Goble | 606/96 |
| 5,163,940 | 11/1992 | Bourque | 606/96 |

FOREIGN PATENT DOCUMENTS 221356 4/1985 Fed. Rep. of Germany ........ 606/98

OTHER PUBLICATIONS

M. Kurosaka, "The Crucial Choice for Winning Results", DePuy ®, 1989, six pages.

Primary Examiner—Stephen C. Pellegrino
Assistant Examiner—Guy V. Tucker
Attorney, Agent, or Firm—Barnes & Thornburg

[57] ABSTRACT

A drill guide is provided for aligning and installing a transverse pin through a tunnel formed by a tunnel drill in a bone to secure a ligament replacement to the bone. The drill guide includes an arm member and a drill guide sleeve coupled to the arm member. The drill guide sleeve is formed to include a central bore for guiding a drill to form a transverse guide hole in the bone to guide insertion of the transverse pin into the bone. The central bore of the drill guide sleeve has an axis which is aligned to intersect the tunnel. The arm member of the drill guide is coupled to the tunnel drill while the tunnel drill is still in the bone to align the arm member and drill guide sleeve at a desired anatomical location using the tunnel drill in the bone as a reference.

27 Claims, 6 Drawing Sheets

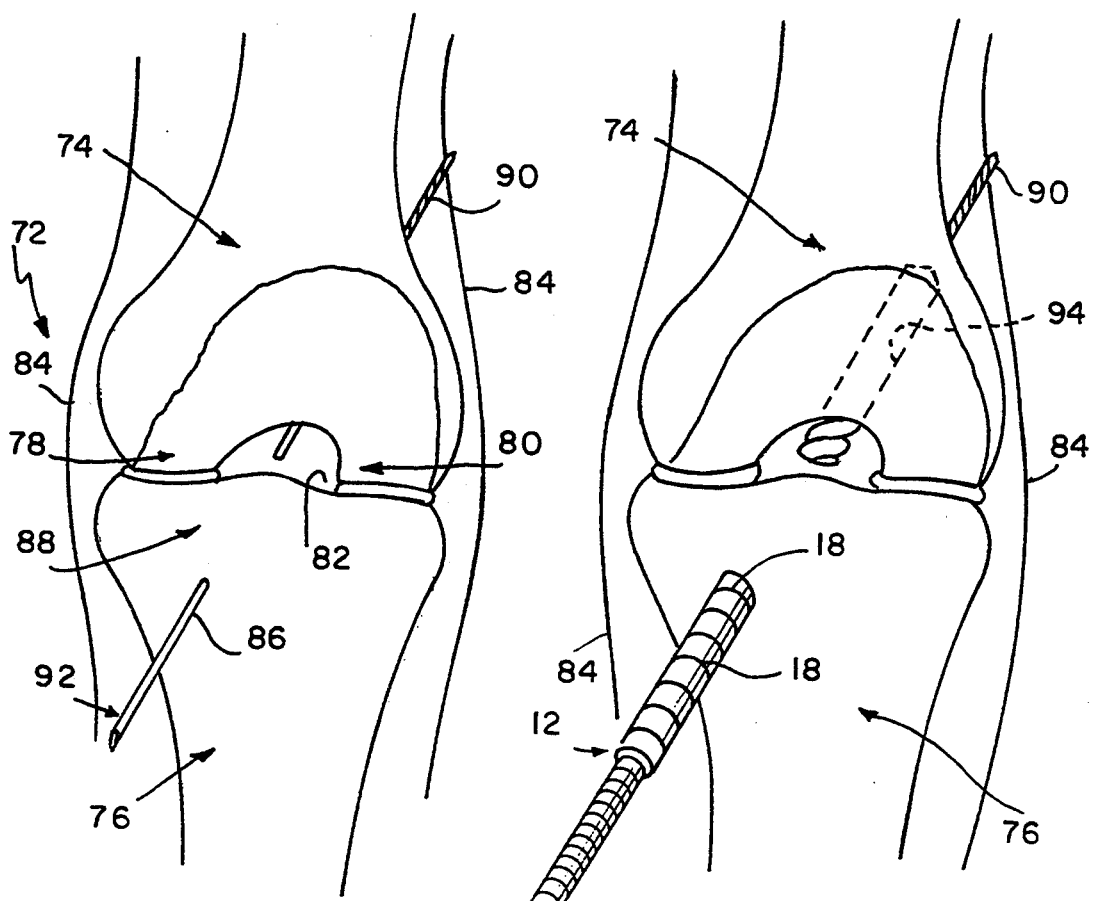

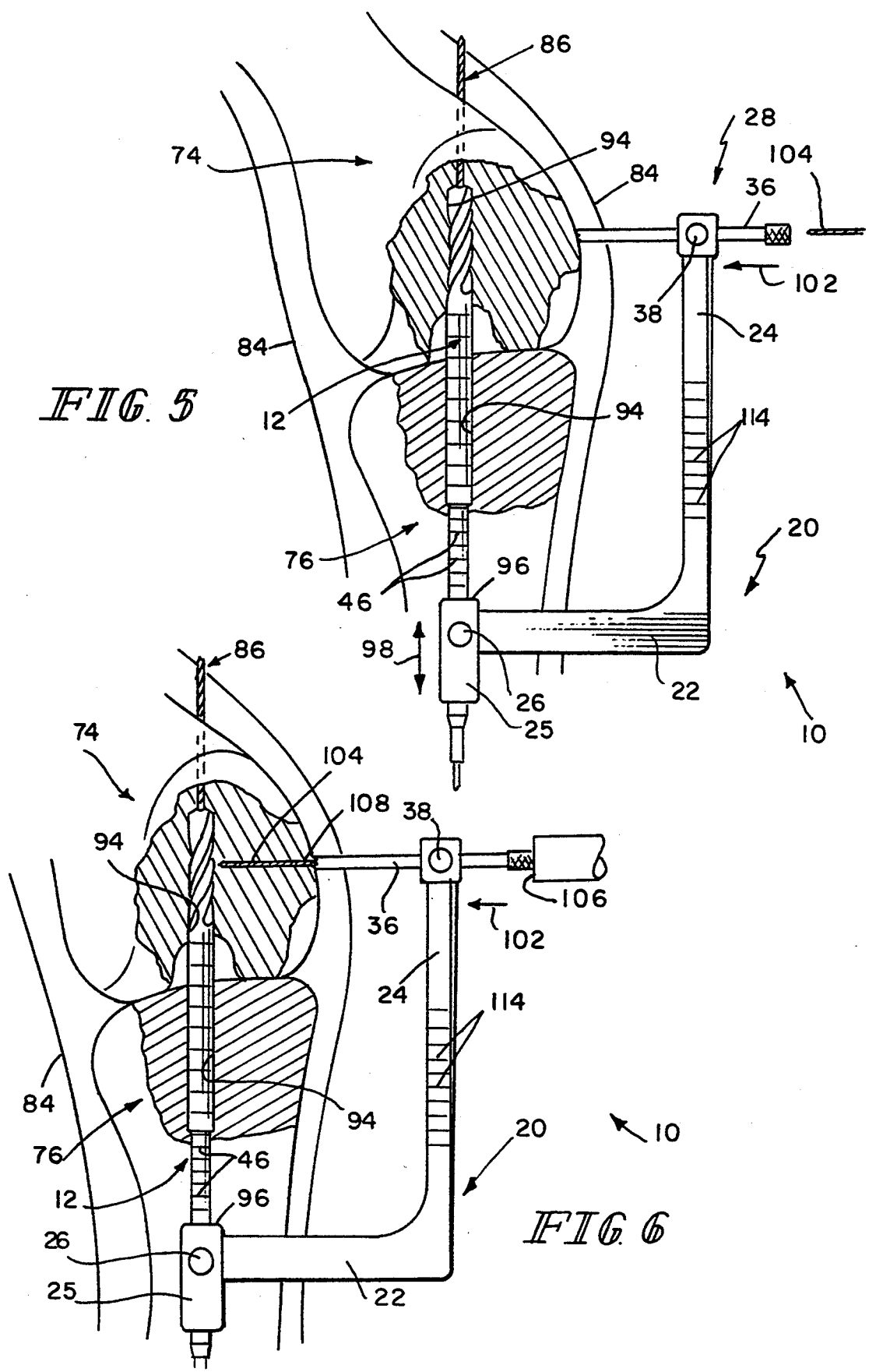

DRILL GUIDE APPARATUS FOR INSTALLING A TRANSVERSE PIN

BACKGROUND AND SUMMARY OF THE INVENTION

The present invention relates to a drill guide apparatus for locating and installing a transverse pin for holding a ligament replacement in a tunnel of a receptor bone. More particularly, the present invention relates to a drill guide apparatus for aligning the pin relative to the tunnel so that the pin intersects the tunnel and the ligament replacement to secure the ligament replacement to the bone to promote healing and bonding of the ligament replacement.

When a ligament such as an anterior cruciate ligament (ACL) of a knee is damaged or torn, a replacement ligament is often installed in the knee to reconstruct the natural anterior cruciate ligament. During such reconstruction, a tunnel is typically drilled through the anterior portion of the tibia upwardly through the tibial plateau and into the distal end of the femur to approximate the natural position of the anterior cruciate ligament. A bone-ligament-bone graft is then harvested, often from the patellar tendon following standard grafting procedures. Typically a wedge-shaped graft is cut and contoured using a graft guide. Sutural holes are then formed in the graft. The graft is then installed into the drill tunnel.

Various methods are known for securing the graft within the tibia and femur until the graft can heal. One such method is the use of a Kurosaka TM fixation screw. The Kurosaka TM screw provides an interference fit inside the tunnel with the graft so that the graft is wedged against the wall of the tunnel. See, for example, U.S. Pat. No. 4,950,270.

In other known methods, sutures coupled to the graft are anchored to the bone using screws or washers. The ligaments can also be coupled directly to the bone using plates or washers.

The prior art also includes several different types of drill guides for forming tunnels in the femur and tibia for aligning and installing transverse pins to anchor ligament replacements. One example is U.S. Pat. No. 4,901,711 which shows such a drill guide which mounts on a K-wire after it is inserted into the knee joint. The K-wire exits the knee joint at a point below the tibia and at another point above the femur. The drill guide of the '711 patent is journalled on the K-wire so that the guide is rotatable about the axis of the K-wire. The guide then has a drill sleeve which moves longitudinally parallel to the axis of the K-wire to a selected point to locate a transverse anchoring pin. The drill guide of the present invention is an improvement over the drill guide shown in the '711 patent because the guide is mounted only below the tibia plateau on the shank of the tunnel drill and, of course, the tunnel itself is drilled before the guide used. The drill guide of the present invention uses the tunnel drill as a reference to locate and install a transverse anchoring pin at a selected point. This selected point is established on the drill itself such that the drill guide, when mounted on the drill, and moved to an appropriate scale point on the drill, will locate the transverse pin at an appropriate location below the uppermost end of the tunnel.

Another example is U.S. Pat. No. 4,985,032 which shows a drill guide for locating transverse pins for holding ligaments in tunnels formed in knee joints, particularly to replace the ACL. The U-shaped guide of the '032 patent is used with one leg of the guide inserted upwardly through the tunnel after the drill is removed. Use of the U-shaped guide of the '032 patent requires extra steps which are eliminated by using the tunnel drill itself as a mount for the drill guide. The tunnel drill of the present invention is provided with scale means so that the surgeon will know exactly where the uppermost end of the drill and tunnel are and where the transverse pin has to be located in the femur properly to intersect any ligament replacement placed in the tunnel and pulled upwardly to that innermost end.

The drill guide apparatus of the present invention therefore provides several advantages over these known drill guides. One advantage is that the drill guide of the present invention uses the tunnel drill which forms the tunnel in a bone as a reference axis for establishing the position of transverse guide pins which intersect the tunnel and the replacement ligament to secure the replacement ligament to the bone. The tunnel drill provides a stable reference axis for aligning the pins to intersect the tunnel. In addition, the drill guide can be used right after the tunnel is formed in the bone without the need to insert another rod or other apparatus into the tunnel of the bone.

According to one aspect of the present invention, a drill guide is provided for aligning and installing a transverse pin through a tunnel formed by a tunnel drill in a bone to secure a ligament replacement to the bone. The drill guide includes an arm member and a drill guide sleeve coupled to the arm member. The drill guide sleeve is formed to include a central bore for guiding a drill to form a transverse guide hole in the bone to guide insertion of the transverse pin into the bone. The central bore of the drill guide sleeve has an axis which is aligned to intersect the tunnel. The drill guide also includes means for coupling the arm member to the tunnel drill while the tunnel drill is still in the bone to align the arm member and drill guide sleeve at a desired anatomical location using the tunnel drill in the bone as a reference.

In the illustrated embodiment, the drill guide has generally L-shaped body including a first arm extending in a direction normal to the tunnel drill and a second arm having a proximal end coupled to the first arm so that the second arm extends generally parallel to the tunnel drill and a distal end. The drill guide sleeve is coupled to the distal end of the second arm.

Also in the illustrated embodiment, the coupling means includes means for mounting the arm member on the tunnel drill for movement longitudinally along an axis of the tunnel drill to position the drill guide sleeve relative to an uppermost end of the tunnel drill and the tunnel end formed thereby. The arm member is also rotatable about the tunnel drill axis to position the drill guide sleeve to a selected anatomical position relative to the bone. The drill guide also includes means for indicating the position of the drill guide sleeve relative to an uppermost end of the tunnel drill which corresponds to an end of the tunnel.

According to another aspect of the invention, the drill guide further comprises a second drill guide sleeve slidably coupled to the arm member of the drill guide. The second drill guide sleeve is formed to include a central bore for guiding the drill to form a second transverse guide hole in the bone to guide insertion of a second transverse pin into the bone. The central bore of the second drill guide sleeve has an axis which is aligned to intersect the tunnel.

In the illustrated embodiment, the arm member of the drill guide is twisted at a predetermined angle to align the second guide sleeve relative to the tunnel drill so that the axis of the second guide sleeve intersects the tunnel. The drill guide further includes means for indicating the distance between the first and second drill guide sleeves.

According to yet another aspect of the invention, the drill guide sleeve is coupled to the arm member by a ratchet mechanism for selectively axially positioning the drill guide sleeve relative to said arm member. In the illustrated embodiment, the ratchet mechanism includes a spring loaded cog configured to engage the drill guide sleeve. The spring loaded cog permits axial movement of the drill guide sleeve relative to the arm member in a direction toward the bone and prevents axial movement of the drill guide sleeve relative to the arm member in a direction away from the bone. The drill guide sleeve is formed to include a plurality of teeth for engaging the spring loaded cog to lock the drill guide sleeve in a selected axial position relative to the arm member. The second drill guide sleeve is also coupled to the arm member by a ratchet mechanism for selectively axially positioning the second drill guide sleeve relative to said arm member.

The drill guide apparatus of the present invention is used to locate and install transverse pins for holding a ligament replacement in a tunnel formed in a bone with the pin intersecting the tunnel and the ligament replacement. When used to secure a replacement ligament for an anterior cruciate ligament, the tunnel is drilled through the tibia plateau upwardly into the distal end of the femur.

The drill guide is installed over the drill used in the tunnel drilling step. The drill guide is rotatable about the axis of the tunnel drill. The drill guide has a journal end mounted on the drill and an upwardly extending arm terminating with a transverse guide opening having an axis intersecting the axis of the tunnel drill. The position of the drill guide is adjusted longitudinally on the drill to position the axis of the transverse guide opening relative to the uppermost end of the tunnel corresponding to a preselected point at upper end of the drill to intersect the ligament replacement in the tunnel. The position of the drill guide is also adjusted by pivoting the drill guide about the axis of the axis of the drill to find a desired anatomical location for inserting the transverse pin into the femur. A drill sleeve in the transverse guide opening is then moved into engagement with the femur. Using the drill sleeve as a guide and using a first drill having a first diameter, a transverse guide hole is drilled transversely into the femur a predetermined distance stopping short of the tunnel to provide a transverse guide hole. The first drill is then removed from the drill sleeve, and a second drill having a second diameter larger than the first diameter is then inserted into the guide hole. The drill sleeve is then removed from the drill guide, leaving the second drill in place in the guide hole in the femur.

If it is desired to insert a transverse pin through the replacement ligament in the tibia, the position of the drill guide is adjusted about the axis of the drill to position a tibia drill guide at a desired anatomical location for inserting the second transverse pin into the tibia. A drill sleeve of the tibia drill guide is inserted in a second transverse guide opening provided on said upwardly extending arm and moved into engagement with the tibia. Using the drill sleeve as a guide and using the first drill having the first diameter, a transverse guide hole is drilled in the tibia a predetermined distance short of the tunnel. The first drill is then removed from the drill sleeve. A third drill having a diameter substantially equal to the second and larger diameter is then inserted into the guide hole of the tibia. The drill sleeve is then removed leaving the third drill in place in the guide hole in the tibia.

The drill guide and the tunnel drill are removed from the knee and the ligament replacement is inserted into the tunnel in the femur and tibia. A soft tissue protector is installed over the second drill to engage the femur. Then, using the second drill, a hole is drilled through the femur, the tunnel, the ligament replacement and on into the femur on an opposite side of the tunnel. The second drill is then removed leaving the soft tissue protector. Finally, the transverse pin is inserted through soft tissue protector, the guide hole, the tunnel, the ligament replacement therein, and on into the femur on an opposite side of the tunnel to anchor the ligament replacement in the femur.

A soft tissue protector is then inserted over the third drill to engage the tibia. Using the third drill, a hole is drilled through the tibia, the tunnel in the tibia, the ligament replacement and on into the tibia on an opposite side of the tunnel. The third drill is then removed leaving the soft tissue protector. The transverse pin is then inserted through the soft tissue protector, the tibia guide hole, the tunnel, the ligament replacement therein and on into the tibia on an opposite side of the tunnel, to anchor the ligament replacement in the tibia.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which:

FIG. 3 is a diagrammatical illustration of a front view of a knee in which the anterior cruciate ligament is to be replaced illustrating a guide pin inserted through an anterior portion of the tibia upwardly through the tibia plateau and through a distal end of a femur to establish the position of a tunnel to be formed through the knee;

FIG. 4 is a diagrammatical illustration similar to FIG. 3 in which a tunnel drill has been inserted over the guide pin in the knee to form the tunnel for receiving the replacement ligament;

FIG. 5 is a diagrammatical illustration of the knee of FIGS. 3 and 4 in which the knee has been canted and the drill guide of FIG. 1 has been installed onto an end of the tunnel drill for aligning the position of a transverse pin for securing the replacement ligament inside the tunnel;

FIG. 6 is a view similar to FIG. 5 in which a first drill is used to form a transverse guide hole through the femur;

DETAILED DESCRIPTION OF THE DRAWINGS

Figure 1:
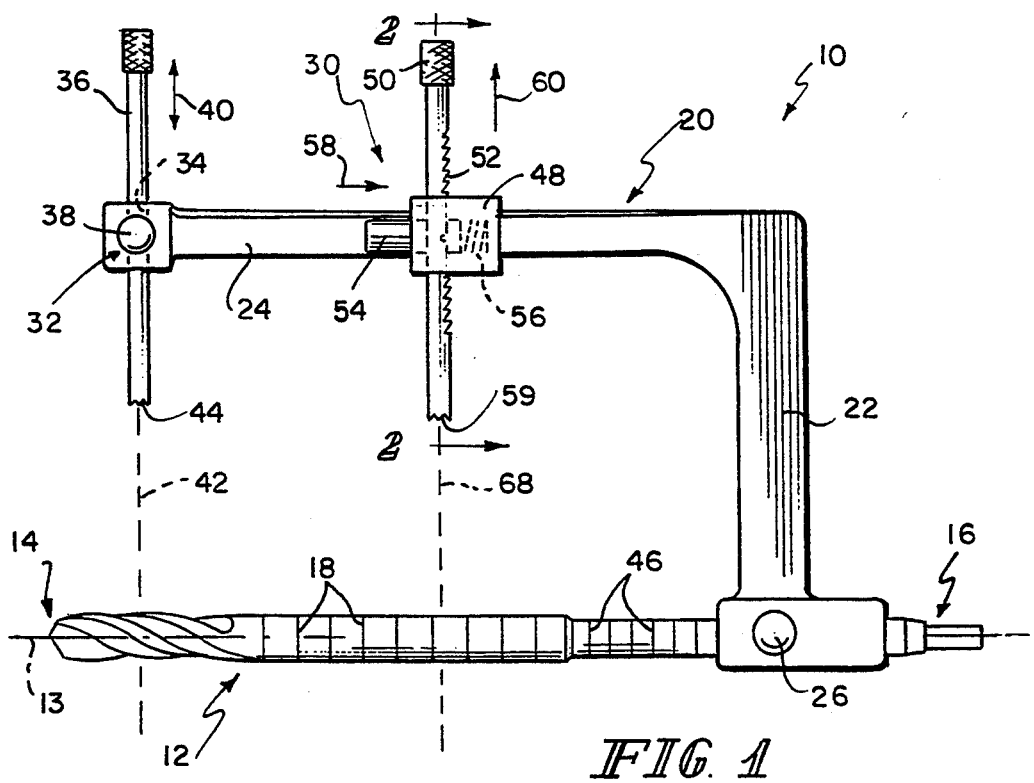
FIG. 1 is an elevational view of a drill guide apparatus of the present invention for aligning and installing transverse pins through a tunnel in a bone using a drill which forms the tunnel as a reference.
Figure 2:
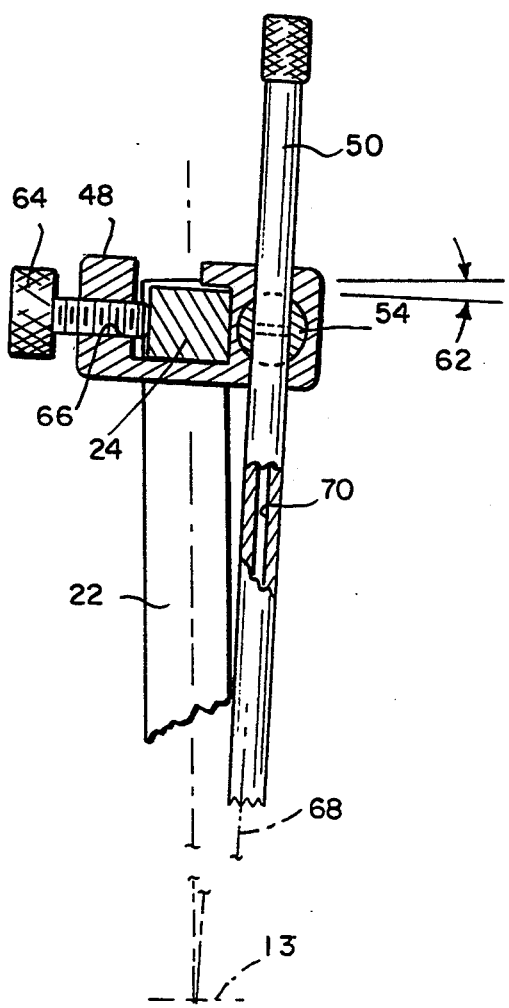
FIG. 2 is a sectional view taken along lines 2—2 of FIG. 1 illustrating a tibia drill guide and drill sleeve aligned at an angle to intersect an axis of the tunnel drill.
Figure 7:
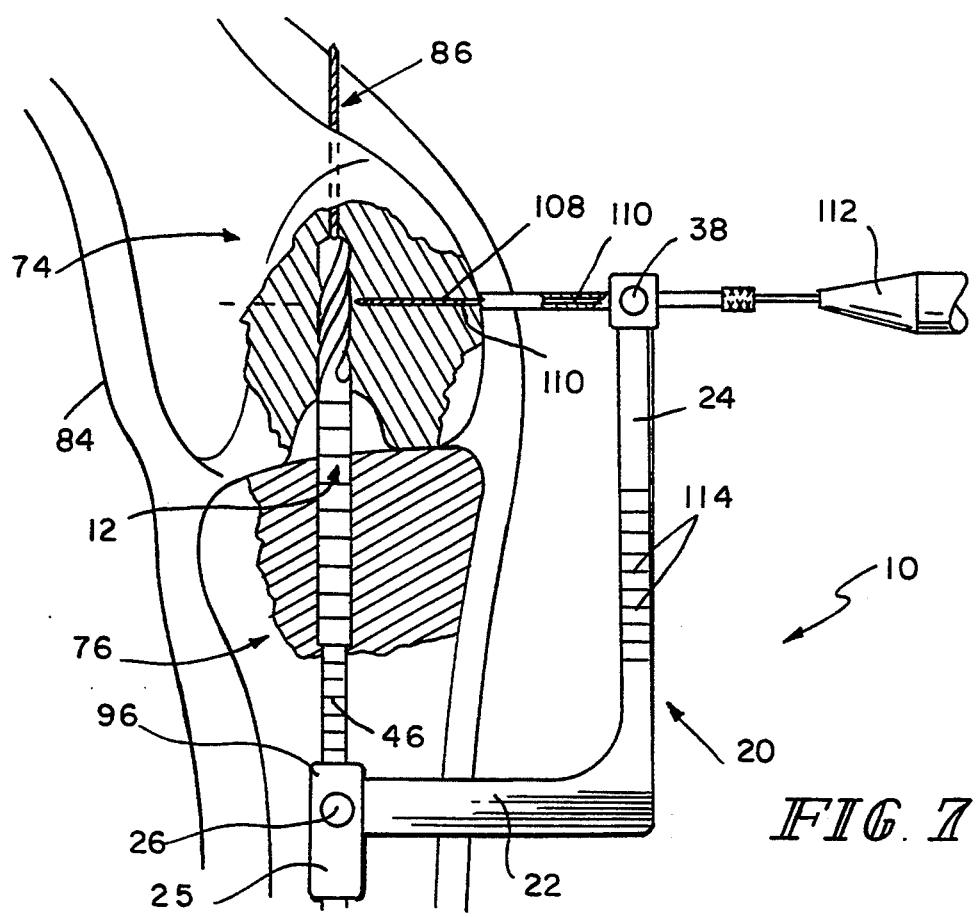
FIG. 7 is a diagrammatical illustration similar to FIGS. 5 and 6 in which a second drill is inserted through the drill sleeve to a position below the arm of the drill guide.

Referring now to the drawings, FIGS. 1 and 2 illustrate a drill guide apparatus 10 of the present invention. A tunnel drill 12 is used to form a tunnel through a bone such as through the tibia and femur to replace the anterior cruciate ligament in a knee joint. Tunnel drill 12 includes a first end 14 for cutting through the bone and a second end 16 for attachment to a driver. Drill 12 includes a depth indicator scale or marks 18 which are labeled with numbers to indicate the distance from the marks 18 to the tip of first end 14 of drill 12. Drill guide apparatus 10 is adapted to be rotatably and slidably coupled to second end 16 of drill 12. Drill guide apparatus 10 illustratively includes a generally L-shaped body portion 20 having a first arm 22 extending generally perpendicular to drill 12 and a second arm 24 which extends away from first arm 22 in a direction generally parallel to drill 12. An end of first arm 22 is slidably and rotatably coupled to second end 16 of drill 12 by a spring-loaded cog 26 inside a connector body 25. Cog 26 can be depressed to permit sliding movement of body portion 20 of drill guide apparatus 10 longitudinally relative to drill 12. When cog 26 is released, a spring biases cog 26 against annular grooves formed in drill 12 to secure the body portion 20 in a set position relative to drill 12.

Drill guide apparatus 10 includes a femur drill guide 28 and a tibia drill guide 30. Drill guide apparatus 10 is illustratively configured to align and install transverse pins through the femur and tibia which intersect the axis of the tunnel drilled by drill 12 and the replacement ligament located inside the tunnel. Femur drill guide 28 is illustratively integrally formed on a distal end 32 of body portion 20. Transverse guide opening 34 is provided in distal end 32 of body portion, and a drill sleeve 36 extends through transverse guide opening 34. Drill sleeve 36 is slidably coupled to distal end 32 of body portion 20 by a spring-loaded cog 38. Spring-loaded cog 38 may be depressed to permit slidable movement of drill sleeve 36 in the direction of double-headed arrow 40. Drill sleeve 36 includes a plurality of teeth (not shown) on a side opposite the illustrated side in FIG. 1. When cog 38 is released, a spring biases cog 38 against the teeth to secure the drill sleeve in a predetermined position relative to body portion 20. The teeth and cog apparatus provide ratchet means for adjusting the position of drill sleeve 36 relative to body portion 20. Advantageously, drill sleeve 36 may be adjusted relative to body portion 20 using a single hand. This permits accurate and rapid adjustment of the position of drill sleeve 36 as discussed in detail below. Drill sleeve 36 is formed to include a central bore therethrough having an axis 40 which intersects axis 13 of drill 12. The bone engaging end of drill sleeve 36 includes teeth 44 which cut into bone to help hold the position of drill sleeve 36 relative to a bone.

Drill 12 includes a second set of cross hatch markings 46 which provide indicia of the position of axis 42 of drill sleeve 36 relative to the tip of first end 14 of drill 12. The tip of first end 14 of drill 12 corresponds to the position of the end of the tunnel inside the bone. Therefore, a surgeon can use the indicia marks 46 to establish the position for the transverse pin a predetermined distance from the end of the tunnel.

Drill guide apparatus 10 also includes a tibia drill guide 30. Tibia drill guide 30 includes a mounting block 48 and a drill sleeve 50. Drill sleeve 50 includes a plurality of teeth or saw toothed serrations in drill sleeve 36. Mounting block 48 includes a spring-loaded cog 54 and a spring 56 which biases the cog 54. When cog 54 is depressed in the direction of arrow 58, drill sleeve 50 is released to permit slidable movement of drill sleeve 50 relative to body portion 20 in the direction of double-arrow 60. When cog 54 is released, spring 56 biases cog 54 against the teeth 52 of drill sleeve 50 to hold drill sleeve 50 in place relative to body portion 20. In other words, drill sleeve 50 is ratcheted to body 20 in the same manner as drill sleeve 36.

Ratchet control of drill sleeves 36 and 50 provides an advantage of the present invention. This ratcheting feature may be incorporated onto other guide mechanisms which include a guide arm. A push button release (cogs 38 and 54) permits drill sleeves 36 and 50 to slide back and forth relative to arm 24. This provides better control of movement of drill sleeves 36 and 50 when compared to drill sleeves which are coupled to guide arms by a screw fastener. The ratchet mechanisms also provide a more positive lock for drill sleeves 36 and 50 against the bone. The ratchets provide a one-way lock and can be pushed toward the bone but not pulled away from the bone. Therefore, they can be moved with one hand. The ratchet mechanism also keeps a tight engagement between teeth 44 and 46 of drill sleeves 36 and 50, respectively, against the bone. It is understood that other ratchet mechanisms other than spring-loaded cogs 38 and 54 may be used in accordance with the present invention. It is also understood that the ratchet mechanism can be used with other drill guides for forming holes or tunnels through a bone. Therefore, the ratchet mechanism feature is not limited to the drill guide apparatus 10 of the present invention.

As illustrated in FIG. 2, arm 24 of body portion 20 is twisted a predetermined angle relative to arm 22 illustrated by angle 62. Illustratively, angle 62 is about 5.8 degrees. Body portion 48 is slidably coupled to arm 24 by a threaded bolt 64 extending through a threaded aperture 66 in body portion 48. By providing the twisted arm 24, an axis 68 defined by longitudinal bore 70 of drill sleeve 50 intersects axis 13 of drill 12.

Drill guide apparatus 10 is used to align and install transverse pins into a tunnel formed in a bone. Operation of the drill guide apparatus 10 of the present invention is illustrated in FIGS. 3–11. The drill guide apparatus 10 is particularly suited for replacement of an anterior cruciate ligament in a knee joint. However, it is understood that the drill guide apparatus may be used to replace other ligaments in a bone. Detailed operation of the drill guide apparatus 10 will be explained with reference to replacing the anterior cruciate ligament in a knee joint.

As illustrated in FIG. 3, a knee joint 72 includes a femur bone 74 and a tibia bone 76. Condyles 78 and 80 of femur 74 articulate against a tibial plateau during movement of knee 72. FIGS. 3–11 also diagrammatically illustrate soft tissue 84 surrounding the knee. During replacement of the anterior cruciate ligament, a tunnel is formed through the knee joint at an angle to replicate the position of the natural anterior cruciate ligament. Therefore, the first step for replacing the anterior cruciate ligament of a knee is to form the tunnel through the knee 72 for receiving a replacement ligament. The first step for drilling the tunnel is typically to install a K-wire or guide pin 86 through an anterior portion 88 of tibia 76 upwardly through tibial plateau 82 and on upwardly through the distal end of femur 74. The position of guide pin 76 can be viewed using endoscopes inserted into the knee or using x-rays or fluoroscopes. If the surgeon is unhappy with the position of guide pin 86, it can be removed and re-inserted without causing substantial damage to knee 72. This because guide pin 86 cuts only a relative thin hole through knee joint 72. Guide pin 86 includes a first end 90 equipped with a drill point for cutting the bone and a second end 92 which includes an aperture 94 which permits the guide pin 86 to pull the replacement ligament through the tunnel as discussed in detail below.

After the surgeon has positioned the guide pin 86 at a desired location for the center line of the tunnel, drill 12 is used to form the tunnel in knee joint 72. Preferably, drill 12 is cannulated so that drill 12 can pass over guide pin 86 to cut tunnel 94 through knee joint 72. Therefore, guide wire 86 provides the center line for tunnel 94. FIG. 4 illustrates drill 12 which has been driven into knee joint 72 along the path established by guide wire 86 to form tunnel 94.

After tunnel 94 is formed inside knee joint 72, the surgeon leaves drill 12 in place in the knee. The driver is removed from drill 12 and drill guide apparatus 10 is inserted over second end 16 of drill 12. A surgeon can read the depth of insertion of drill 12 into the bone by reading the depth indicia marks 18 on drill 12. This gives the surgeon an estimate of the length of the replacement ligament required. The replacement ligament is typically harvested in a conventional manner using known techniques. For instance, a portion of the patellar tendon can be harvested to provide tissue for replacing the anterior cruciate ligament, the tissue being a length of tendon with a bone plug at each end.

Other types of ligament replacements are being considered and some are actually being used. In this specification and in the appended claims, the term "ligament replacement" is intended to refer to any material which may be harvested from the patient, from cadavers, or from animals or any material which may be made, for instance, from plastic or metal to provide a ligament function. Further, in this specification and in the appended claims, the term "intersecting the ligament replacement" is intended to refer to all types of intersection and/or connection which may be accomplished by extending a pin transversely through a tunnel. For example, as indicated, such a transverse pin may extend through the bone plug provided on the end of a patella tendon. The transverse pin may extend through the soft tissue itself or through a loop formed in the soft tissue. Still further, the word "transverse" is intended to mean an intersection or crossing which may or may not be perpendicular to the tunnel axis.

After the replacement ligament is harvested or obtained, a surgeon can estimate the distance from an end of the bone plug which would be optimum for inserting the transverse pin (if the bone plug is the selected type of ligament replacement). Drill guide apparatus 10 permits the position of the pins to be aligned at about the optimum position. By depressing cog 26, the drill guide apparatus 10 can slide back and forth in the direction of double-headed arrow 98 on drill 12.

If the surgeon knows the optimum location to insert the transverse pin, the surgeon sets the position of drill guide on drill 12 to that known distance on indicia marks 46. For instance, if the surgeon wants to position the transverse pin 25 mm from the end of the replacement ligament, the surgeon slides drill guide apparatus 10 until a top edge 96 of connector block 25 is aligned with the measurement mark 46 corresponding to 25 mm. This positions the axis 42 of femur drill sleeve 36 at a distance 25 mm from the end 14 of drill 12. Since the end 14 of drill 12 will correspond to the end of the replacement ligament, the axis 42 of drill sleeve 30 would be 25 mm from the end of the replacement ligament. Therefore, the position of drill guide apparatus 10 can be selectively adjusted longitudinally on the drill to position the axis of the transverse guide opening and drill sleeve 36 relative to the uppermost end of the tunnel corresponding to a preselected point at the upper end of the drill so that the axis will intersect ligament replacement in the tunnel.

Figure 11:
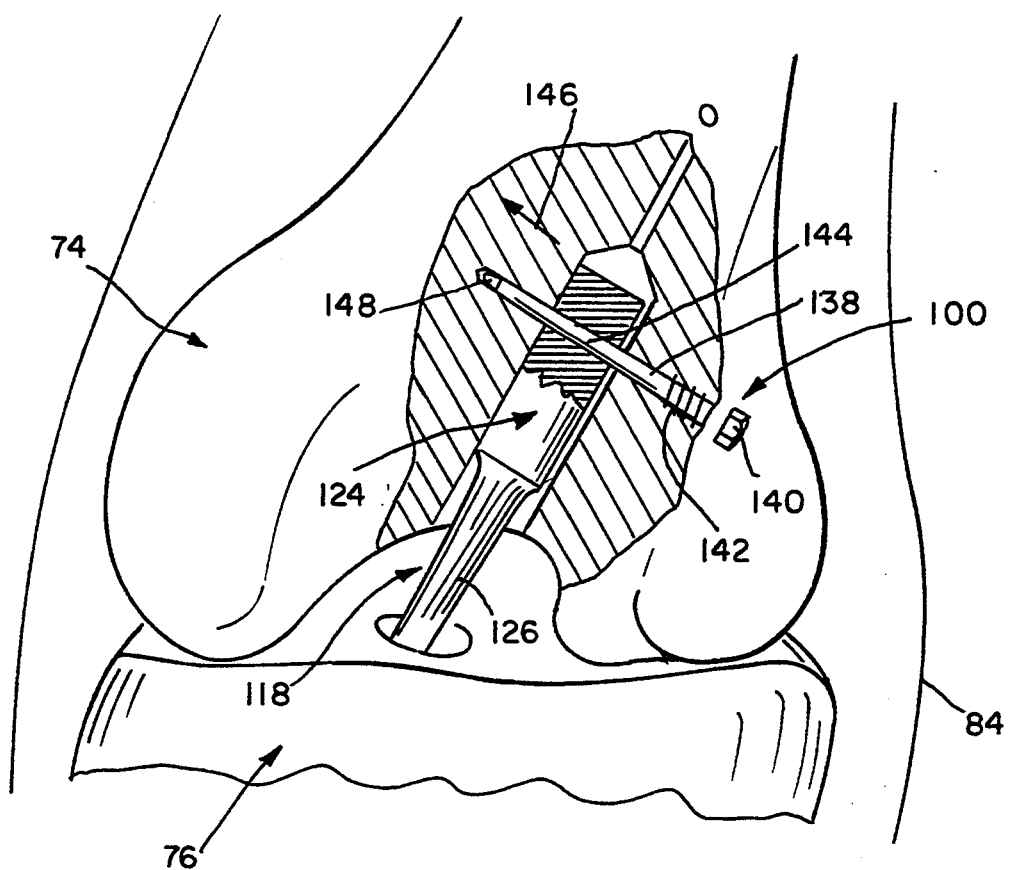
FIG. 11 is a diagrammatical illustration with portions broken away illustrating a transverse pin installed through the hole formed by the second drill to extend through the femur, through the tunnel and the replacement ligament therein, and on into the femur on the opposite side of the tunnel to secure the replacement ligament to the femur.

After the longitudinal position of drill guide apparatus 10 is set, the next step is to rotate or pivot drill guide apparatus 10 about the axis of drill 12 and guide pin 86 to position drill sleeve 36 at a desired anatomical location for inserting the transverse pin into the femur. Typically, this location is on the lateral epicondyle 100 as best illustrated in FIG. 11.

After the desired anatomical position of the transverse pin has been selected, drill sleeve 36 is ratcheted toward femur in the direction of arrow 102. Drill sleeve 36 passes through a small incision in the soft tissue 84 and engages the surface of femur 72 as illustrated in FIG. 5. A first drill 104 is then used to drill a first hole through femur 74 using drill sleeve 36 as a guide. First drill 104 has a first diameter which is illustratively 2.4 mm. Drill 104 forms a transverse hole in femur 74. A stop 106 FIG. 6 is coupled to drill 104 so that drill 104 drills only a predetermined distance into femur 74. Stop 106 prevents drill 104 from hitting drill 12 located in tunnel 94. Therefore, the end of stop 106 abuts the arm 24 to cause the drill 104 to stop short of tunnel 94 and provides a transverse guide hole 108 through femur 74. The first drill 104 is then removed from drill sleeve 36.

A second drill 110 is then inserted into transverse guide hole 108. Second drill 110 has a second diameter which is slightly larger than the first diameter. Illustratively, the diameter of second drill 110 is about 2.5 mm. Second drill 110 is tapped through drill sleeve 36 and into transverse guide hole 108 with an insertion device 112 which inserts second drill 110 to a depth so that an end of second drill 110 is located beyond end 32 of body portion 20. Drill sleeve 36 is then removed from body portion 20 leaving drill 110 in femur 74. Drill 110 therefore marks the position of the transverse guide hole 108 through soft tissue 84 so that a surgeon can easily locate the hole 108.

Figure 8:
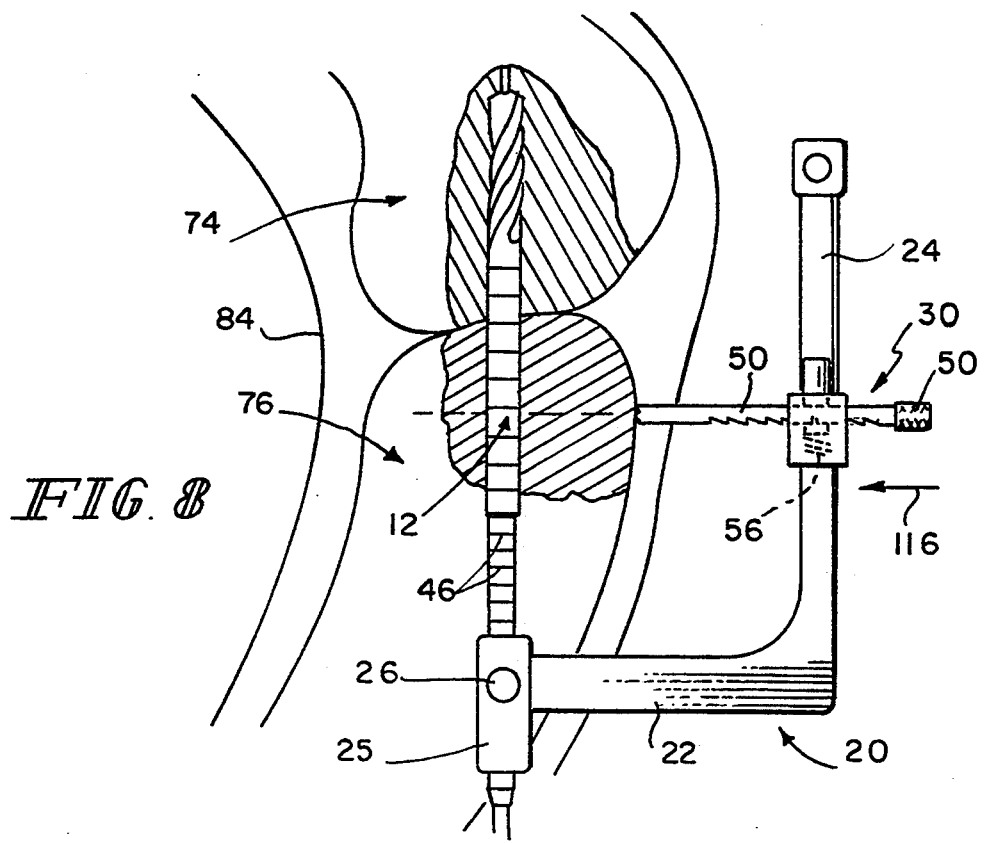
FIG. 8 is a diagrammatical illustration of the knee in which the knee has been rotated 90° with respect to FIGS. 3 and 4 and a tibia drilling guide is used to establish the desired anatomical position for installing a transverse pin through the tunnel in the tibia.
Figure 9:
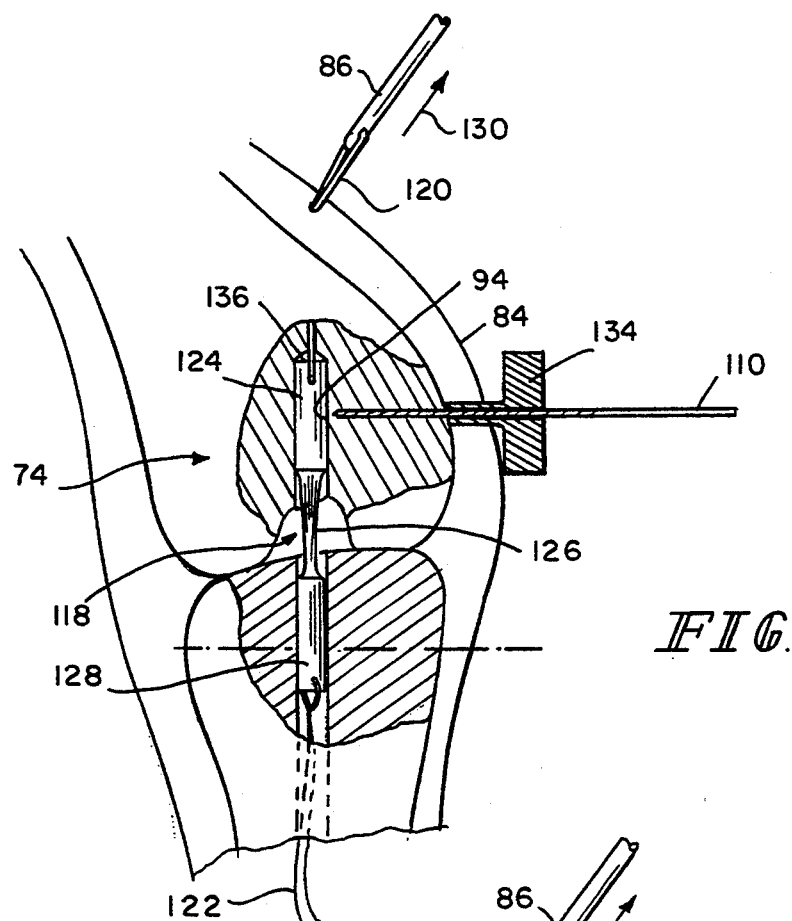
FIG. 9 is a diagrammatical view similar to FIGS. 5-7 in which the tunnel drill and drill guide have been removed, a replacement ligament has been inserted into the tunnel, and a soft tissue protector has been installed over the second drill remaining in the femur.

If it is desired to secure the ligament replacement in the tibia with a transverse pin, the drill guide apparatus 10 can be rotated about axis 13 of drill 12 to another position for forming the hole for insertion of the tibia transverse pin. Body portion 20 of drill guide apparatus 10 includes a measurement scale including labeled marks 114. These marks 114 indicate the distance from axis 42 of drill sleeve 36 to axis 68 of drill sleeve 50. Therefore, a surgeon can measure the distance from the optimum location of the transverse pin in the femoral portion of ligament replacement to the optimum position of the transverse pin in the tibial portion of the replacement. Once this distance is known, the surgeon can set the position of tibial drill guide 30 at a location aligned with the mark 114 corresponding to that distance. Once the position of tibia drill guide 30 is set, drill guide apparatus 10 is rotated to align drill sleeve 50 with a desired anatomical location for inserting transverse pin into tibia 76 as illustrated in FIG. 8. Drill sleeve 50 is then ratcheted in the direction of arrow 115 until teeth 59 engage tibia 76. After the drill sleeve 50 is in contact with tibia 76, the surgeon follows the same steps for inserting the drills 104 and 110 into the femur illustrated in FIGS. 6 and 7. First, the small drill 104 is used with a stop 106 to form a transverse guide hole in tibia 74. The guide hole in tibia 74 stops just short of hitting drill 112. A third drill identical to the drill 110 remaining in femur 74 is then tapped into transverse guide hole using instrument 112 illustrated in FIG. 7. After the larger diameter drill is tapped into the guide holes in tibia 76, the drill guide apparatus 10 and tunnel drill 12 are removed. The larger drill remains inside tibia 76 to mark the position of the transverse guide hole in tibia 76 through soft tissue 84 so that a surgeon can easily locate the hole in tibia 76.

In one method of the present invention, a bone-ligament-bone replacement ligament 118 has sutures 120 and 122 attached to opposite ends. In the embodiment illustrated in FIGS. 9-11, the replacement ligament 118 includes a first bone block 124, an intermediate ligament 126, and a second bone block 128. Sutures 120 may be secured in opening 94 in guide pin 86 so that replacement ligament 118 can be pulled into tunnel 94 as guide pin 86 is removed from tunnel 94 in the direction of arrow 130. The sutures 120 are used to hold a top edge 132 of replacement ligament 118 at a location adjacent the uppermost part of tunnel 94.

A soft tissue protector 134 is then inserted over drill 110 which remains in femur 74. Soft tissue protector 134 protects soft tissue 84 from being wrapped around drill 110. In addition, soft tissue protector 134 includes a handle (not shown) and teeth which can be tapped slightly into the femur 74 to mark the position of the guide hole formed by drill 110.

Figure 10:
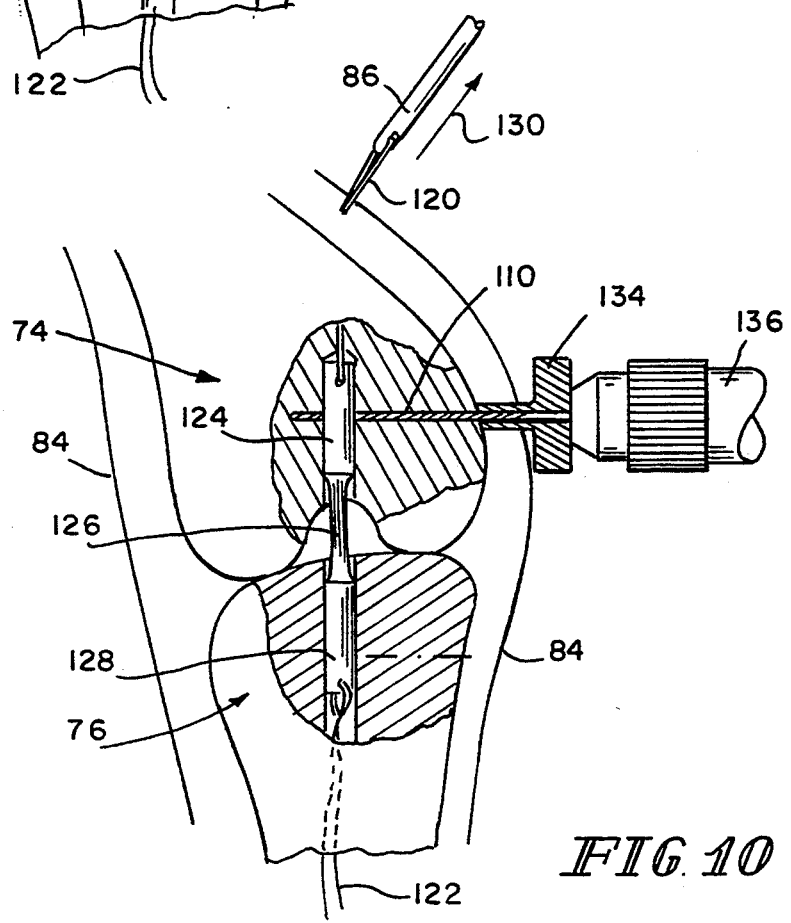
FIG. 10 is a diagrammatical illustration similar to FIG. 9 in which the second drill is used to form a hole through the femur, through the tunnel and the replacement ligament therein, and on into the femur on an opposite side of the tunnel.

The next step of the invention is illustrated in FIG. 10. A driver 136 is used to drive drill 110 further into femur 74, through tunnel 94, through the bone block 124 of replacement ligament 118 located inside tunnel 124, and on into the femur 74 on an opposite side of tunnel 94 from driver 136.

The drill 110 is then removed, leaving soft tissue protector 134 in place. Therefore, after removing drill 110, the soft tissue protector 134 continues to mark the location of hole 108 drilled through femur 74. A transverse pin is then inserted through soft tissue protector 134 and into hole 108. A hex driver is used to drive transverse pin into femur 74. Transverse pin 138 is illustrated in FIG. 11.

Although many types of transverse pins may be used with the present invention, the preferred embodiment includes an external hex head 140, a threaded section located adjacent head 140, and a tapered, generally smooth shank 144. Tapered shank 144 applies a force in the direction of arrow 146 to bone block 124 as cross pin 138 is inserted into femur 74. This forces bone block 124 against an outer wall of femur of tunnel 94 to secure bone block 124 within femur 74 and to promote healing of bone block 124 inside femur 74. Cross pin 138 also includes a blunt tip 148 to facilitate insertion of cross pin 138 into femur 74.

Bone block 128 located inside tibia 76 can be secured in any number of ways. A Kurosaka ™ fixation screw may be inserted into an aperture formed by drill 12 to secure bone block 128 to tibia 76. In addition, sutures 122 can be secured to tibia 76 using an attachment washer.

If it is desired to use a transverse pin through bone block 128 in tibia 76, ligament replacement 118 is adjusted to the proper tension by pulling on sutures 122. The third drill located in the hole formed in tibia 76 as discussed above is then used to establish the transverse guide hole for a second transverse pin which is inserted through the tibia and tunnel 94 and through bone block 128 and on into the tibia on an opposite side from a driver. The transverse pin is inserted into the tibia in the same manner discussed above in detail with reference to drilling and installing the transverse pin in femur 74.

Although the invention has been described in detail with reference to a certain preferred embodiment, variations and modifications exist within the scope and spirit of the invention as described and defined in the following claims.

What is claimed is:

1. A drill guide for aligning and installing a transverse pin through a tunnel formed by a tunnel drill moveable into and along a bone to drill the tunnel to secure and house a ligament replacement therein to the bone, the drill guide comprising:

a tunnel drill insertible into the bone for drilling a straight tunnel along an axis into the bone to house the ligament replacement:

an arm member;

a drill guide sleeve coupled to a part of the arm member, the drill guide sleeve being formed to include a central bore for guiding a drill to form a guide hole in the bone transverse to the straight tunnel to guide insertion of the transverse pin when placed in the guide hole into the bone, the central bore of the drill guide sleeve having an axis which is aligned to intersect the straight tunnel transverse to its longitudinal axis while the tunnel drill is inserted in the bone; and means for coupling the arm member to the tunnel drill for rotational and axial shifting along the tunnel drill to position the drill guide sleeve while the tunnel drill is still in the bone to align the part of the arm member and the drill guide sleeve at a desired anatomical location along the length of the tunnel using the tunnel drill in the bone as a reference.

2. The drill guide of claim 1, wherein the drill guide sleeve is coupled to the part of the arm member by a ratchet mechanism for selectively positioning an end of the drill guide sleeve at a distance spaced from said part of said arm member.

3. The drill guide of claim 2, wherein the ratchet mechanism includes a spring loaded cog configured to engage the drill guide sleeve, the spring loaded cog permitting movement of the end of the drill guide sleeve away from the part of the arm member in a direction toward the bone and preventing movement of the end of the drill guide sleeve toward the part of the arm member in a direction away from the bone.

4. The drill guide of claim 3, wherein the drill guide sleeve is formed to include a plurality of teeth for engaging the spring loaded cog to lock the end of the drill guide sleeve in a selected spaced position relative to the arm member.

5. The drill guide of claim 1, further comprising means for indicating the position of the drill guide sleeve along the part of the arm member relative to a drilling end of the tunnel drill which corresponds to an end of the tunnel.

6. The drill guide of claim 1, further comprising a second drill guide sleeve slidably coupled to the part of the arm member of the drill guide, the second drill guide sleeve being formed to include a central bore for guiding a drill to form a second guide hole in the bone transverse to the straight tunnel to guide insertion of a second transverse pin when placed in the second guide hole into the bone, the central bore of the second drill guide sleeve having an axis which is aligned to intersect the straight tunnel drill transversely to its longitudinal axis while the tunnel is inserted in the bone.

7. The drill guide of claim 6, wherein the part of the arm member of the drill guide is twisted at a predetermined angle to align the second guide sleeve relative to the tunnel drill so that the axis of the second guide sleeve intersects the tunnel.

8. The drill guide of claim 6, wherein the part of the arm member of the drill guide includes means for indicating the distance between the first and second drill guide sleeves.

9. The drill guide of claim 6, wherein the second drill guide sleeve is coupled to the arm member by a ratchet mechanism for selectively positioning an end of the second drill guide sleeve at a distance spaced from said part of said arm member.

10. The drill guide of claim 1, wherein the arm member has a generally L-shaped body including a first arm extending in a direction normal to the longitudinal axis of the tunnel drill and a second arm including the said part of said arm member having a proximal end coupled to the first arm so that the second arm extends generally parallel to the tunnel drill and a distal end, the drill guide sleeve being coupled to the distal end of the second arm.

11. The drill guide of claim 1, wherein the coupling means includes means for mounting the arm member on the tunnel drill for movement longitudinally along the drill and the axis of the tunnel to position the drill guide sleeve relative to an uppermost end of the tunnel drill and the tunnel formed thereby, said arm member also being rotatable about the tunnel drill and the tunnel axis to position said drill guide sleeve to a selected anatomical position relative to the bone.

12. A drill guide for locating and installing a transverse pin for holding a ligament replacement in a tunnel drilled through a bone by a tunnel drill, the drill guide comprising:
   a tunnel drill insertable into the bone for drilling a straight tunnel along an axis into the bone to house the ligament replacement;
   a journal portion;
   an arm member extending at an angle from said journal portion and substantially parallel to the longitudinal axis of the tunnel drill;
   a drill guide sleeve coupled to the arm member, the drill guide sleeve providing a guide opening having an axis intersecting a longitudinal axis of the tunnel drill and the tunnel while the tunnel drill is inserted in the bone;
   means for coupling the journal portion to the tunnel drill for movement longitudinally along the tunnel drill while the tunnel drill is still in the tunnel to position said transverse guide opening of the drill guide sleeve relative to an uppermost end of the tunnel drill and the tunnel formed thereby, said journal portion also being rotatable about the tunnel drill and tunnel axis to position said transverse guide opening to a selected anatomical position relative to the bone.

13. The drill guide of claim 12, wherein the drill guide sleeve is coupled to the arm member by a ratchet mechanism for selectively positioning an end of the drill guide sleeve at a distance spaced from said arm member.

14. The drill guide of claim 13, wherein the ratchet mechanism includes a spring loaded cog configured to engage the drill guide sleeve, the spring loaded cog permitting movement of the end of the drill guide sleeve away from the arm member in a direction toward the bone and preventing movement of the end of the drill guide sleeve toward the arm member in a direction away from the bone.

15. The drill guide of claim 14, wherein the drill guide sleeve is formed to include a plurality of teeth for engaging the spring loaded cog to lock the end of the drill guide sleeve in a selected spaced position relative to the arm member.

16. The drill guide of claim 12, further comprising means for indicating the position of the drill guide sleeve along and relative to a drilling end of the tunnel drill which corresponds to an end of the tunnel.

17. The drill guide of claim 12, further comprising a second drill guide sleeve slidably coupled to the arm member of the drill guide, the second drill guide sleeve being formed to include a central bore for guiding a drill to form a second guide hole in the bone transverse to the axis of the tunnel to guide insertion of a second transverse pin into the bone, the central bore of the second drill guide sleeve having an axis which is aligned to intersect the tunnel transversely to the tunnel axis while the tunnel drill is inserted in the bone.

18. The drill guide of claim 17, wherein the arm member of the drill guide is twisted at a predetermined angle to align the second guide sleeve relative to the tunnel drill so that the axis of the second guide sleeve intersects the tunnel.

19. The drill guide of claim 17, wherein the arm member of the drill guide includes means for indicating the distance between the first and second drill guide sleeves.

20. The drill guide of claim 17, wherein the second drill guide sleeve is coupled to the arm member by a ratchet mechanism for selectively positioning an end the second drill guide sleeve at a distance spaced from said arm member.

21. A drill guide for locating and installing a transverse pin for holding a replacement ligament in a tunnel drilled through a bone by a tunnel drill, the drill guide comprising:
- a tunnel drill insertable into the bone for drilling a straight tunnel along an axis into the bone to house the ligament replacement;
- an arm member extending substantially parallel to the longitudinal axis of the tunnel drill;
- means for guiding a drill to form a guide hole in the bone including a drill guide sleeve aligned to intersect the tunnel axis and the replacement ligament therein transversely and to receive said transverse pin, the guiding means being coupled to the arm member; and
- means for coupling the arm member to the tunnel drill for rotational and axial shifting along the tunnel drill to position the drill guide sleeve while in the tunnel drill is still in the bone to align the drill guide sleeve at a selected anatomical location using the tunnel drill in the bone as a reference.

22. The drill guide of claim 21, further comprising means for indicating the position of the guiding means relative to a drill end of the tunnel drill which corresponds to an end of the tunnel.

23. The drill guide of claim 21, wherein the arm member has a generally L-shaped body including a first arm extending in a direction normal to the tunnel drill and a second arm having a proximal end coupled to the first arm so that the second arm extends generally parallel to the tunnel drill and a distal end, the guiding means being coupled to the distal end of the second arm.

24. The drill guide of claim 21, wherein the coupling means includes means for mounting the arm member on the tunnel drill for movement longitudinally along an axis of the tunnel drill and tunnel to position the guiding means relative to the drill end of the tunnel drill and the tunnel end formed thereby, said arm member also being rotatable about the tunnel drill and tunnel axis to position said guiding means to the selected anatomical position relative to the bone.

25. A drill guide for aligning a drill to form a hole in a bone, the drill guide comprising:
- a tunnel drill insertible in the bone for drilling a straight tunnel along an axis into the bone;
- an arm member;
- a drill guide sleeve formed to include a central bore for guiding a drill to form a hole in the bone that intersects an axis of the tunnel drill and the tunnel transversely;
- a ratchet mechanism for coupling the drill guide sleeve to the arm member to permit selective axial positioning of an end of the drill guide sleeve at a distance spaced from said arm member; and
- means for coupling the arm member to said tunnel drill for rotational and axially shifting along the tunnel drill for aligning the drill guide sleeve with respect to the tunnel drill at a selected anatomical location relative to the bone.

26. The drill guide of claim 25, wherein the ratchet mechanism includes a spring loaded cog configured to engage the drill guide sleeve, the spring loaded cog permitting movement of the end of drill guide sleeve away from the arm member in a direction toward the bone and preventing movement of the end of the drill guide sleeve toward the arm member in a direction away from the bone.

27. The drill guide of claim 26, wherein the drill guide sleeve is formed to include a plurality of teeth for engaging the spring loaded cog to lock the end of drill guide sleeve in a selected position relative to the arm member.

* * * * *